(12) United States Patent
Kim et al.

(10) Patent No.: US 9,562,246 B2
(45) Date of Patent: Feb. 7, 2017

(54) MICROORGANISMS HAVING L-TRYPTOPHAN PRODUCTIVITY AND A METHOD FOR PRODUCTION OF L-TRYPTOPHAN USING SAME

(71) Applicant: CJ Cheiljedang Corporation, Seoul (KR)

(72) Inventors: Hyung Joon Kim, Seoul (KR); Ju No Jang, Seoul (KR); Kyung Rim Kim, Seoul (KR); Keun Cheol Lee, Gyeonggi-do (KR); Young Bin Hwang, Seoul (KR); Hyeong Pyo Hong, Gangwon-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/784,621

(22) PCT Filed: Apr. 16, 2014

(86) PCT No.: PCT/KR2014/003327
§ 371 (c)(1),
(2) Date: Oct. 15, 2015

(87) PCT Pub. No.: WO2014/171747
PCT Pub. Date: Oct. 23, 2014

(65) Prior Publication Data
US 2016/0153014 A1 Jun. 2, 2016

(30) Foreign Application Priority Data

Apr. 16, 2013 (KR) .................. 10-2013-0041547
Apr. 16, 2014 (KR) .................. 10-2014-0045650

(51) Int. Cl.
*C12P 13/22* (2006.01)
*C12N 9/10* (2006.01)

(52) U.S. Cl.
CPC ........... *C12P 13/227* (2013.01); *C12N 9/1077* (2013.01); *C12Y 204/02018* (2013.01); *Y02P 20/52* (2015.11)

(58) Field of Classification Search
None
See application file for complete search history.

(56) References Cited

U.S. PATENT DOCUMENTS 5,939,295 A   8/1999   Dunkak et al.

FOREIGN PATENT DOCUMENTS

| JP | 57-80398 | 5/1992 |
| KR | 10-1992-0009500 B1 | 10/1992 |
| KR | 10-2010-0092765 A | 8/2010 |
| WO | WO 99-49013 A2 | 9/1999 |

OTHER PUBLICATIONS

Hommel, U., et al., 'Purification and characterization of yeast anthranilate phosphoribosyltransferase.' Eur. J. Biochem 1989, 180:33-40.
International Search Report mailed on Aug. 28, 2014 in PCT/KR2014/003327.
O'Gara, J. P., et al., 'Mutations in the *trpD* gene of *Corynebacterium glutamicum* confer 5-methyltryptophan resistance by encoding a feedback-resistant anthranilate phosphoribosyltransferase.' Applied and Environmental Microbiology, Dec. 1995, 61(12):4477-4479.
Aiba et al. Appl. Environ Microbiol, 1982, vol. 43, No. 2, p. 289-297, "New Approach to Tryptophan by *Escherichia coli*: Genetic Manipulation of Composite Plasmids in Vitro".
NCBI Accession No. P07285 https://www.nchi_nlm_nih.gov/protein/P07285.

*Primary Examiner* — Suzanne M Noakes
(74) *Attorney, Agent, or Firm* — Swanson & Bratschun, L.L.C.

(57) ABSTRACT

The present invention relates to a microorganism of the genus *Escherichia* having enhanced L-tryptophan productivity, which has been modified to express yeast anthranilate phosphoribosyltransferase in order to be able to produce L-tryptophan at high concentration, and to a method for producing L-tryptophan, comprising a step of culturing the microorganism. The microorganism of the genus *Escherichia* can produce L-tryptophan, and thus can be advantageously used in the pharmaceutical industry and the feed industry, particularly for animal feed.

6 Claims, 5 Drawing Sheets

Fig. 2

```
S. cerevisiae      MEA LLS TKKLI SPR LSSTDLHDALLVIL LL RCI N DESLSIYT
S. kudriavzevii    MEA LLS TKKLI SPR LSSTDLHDALLVIL LL RCI N DESLSIYT
S. arboricola      MEA LLS TKKLI SPR LSSTDLHDALLVIL LL RCI N DESLSIYT S. cerevisiae      KVSSFLTALRVT LDHKAEYIAEAAKAVLF SDLVDLF
S. kudriavzevii    KVSSFLTALRVC LDHKAEYIAEAAKAVLF SDLVDLF
S. arboricola      KVSSFLTALRVS LDHKAEYIAEAAKAVLF SDLVDLF S. cerevisiae      V LDIVGTGGDGQNTFNVSTSAAIVA GI GLKICKHGGKASTSNSGAGDL
S. kudriavzevii    I LDIVGTGGDGQNTFNVSTSAAIVA GI GLKICKHGGKASTSNSGAGDL
S. arboricola      V LDIVGTGGDGQNTFNVSTSAAIVA GI GLKICKHGGKASTSNSGAGDL S. cerevisiae      IGTLGCDV KVNSSTV LMPDNTFMFLLAPFFHGQ HV KIPF LGIPT
S. kudriavzevii    IGTLGCDI KVNSSTV LMPDNTFLFLLAPFFHGQ HV KIPF LGIPT
S. arboricola      IGTLGCDV KVNSSTV LMPDNTFLFLLAPFFHGQ HV KIPF LGIPT S. cerevisiae      VFNVLGPLLHPVSHV KRILGVYSKELAPEYAKAAALVY SETFIVWGHV
S. kudriavzevii    IFNVLGPLLHPISHV KRILGVYSKELAPEYAKAAALVYP SETFIVWGHV
S. arboricola      IFNVLGPLLHPVSHV RRVLGVYSKELAPEYAKAAALVY SETFIVWGHV S. cerevisiae      GLDEVSPIGKTTVWHIDP         LKTFQLEPSMFGI FHEL CAS
S. kudriavzevii    GLDEVSPIGKTTVWHIDP         LKTFQLEPSMFGI FHEL CAS
S. arboricola      GLDEVSPIGKTTVWHINP         KTFQLEPSMFGI FHEL CAS S. cerevisiae      YGP ENABILKE VLSGKYHLGI  IYDYILMNTAVLYCLSQGHQNMKEE
S. kudriavzevii    YGP ENARILKE ILSGKYHLGI  IYDYILMNTAVLYCLSQGHQNMKEE
S. arboricola      FGT ENABILKE ILSGKYHLGI  VYDYILMNTAVLYCLSQGHQNMKEE S. cerevisiae      IIKAEES  SGNAI SLEHPI  V    - SEQ ID NO. 1
S. kudriavzevii    IIKAEES  SGNAI SLEHPI  V    - SEQ ID NO. 19
S. arboricola      IIKAEES  SGNAI SLEHPI  V    - SEQ ID NO. 20
```

Fig. 3
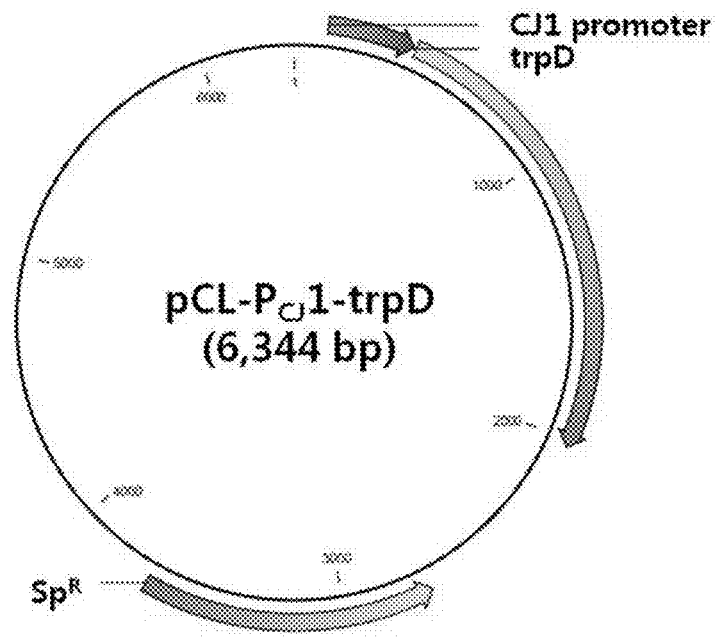
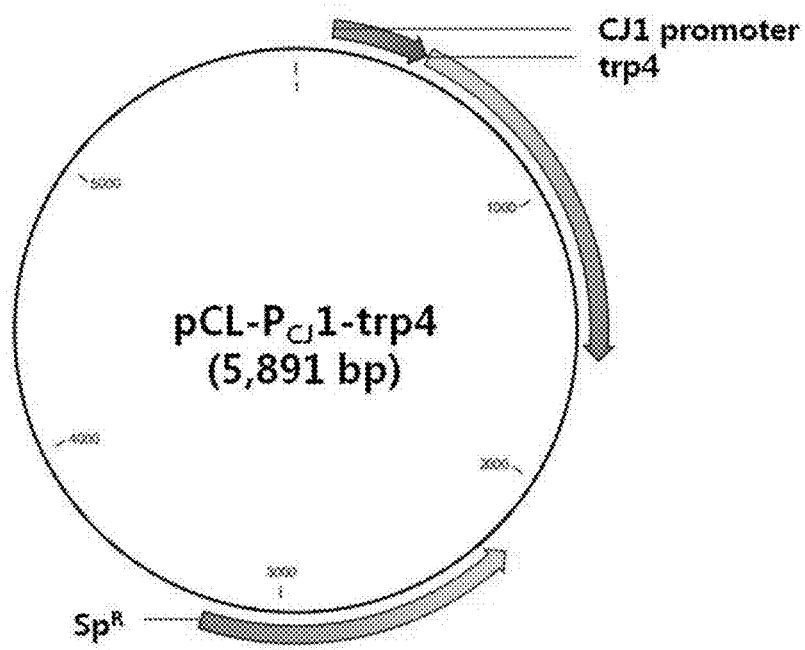

SEQUENCE LISTING

```
<160> NUMBER OF SEQ ID NOS: 20

<210> SEQ ID NO 1
<211> LENGTH: 380
<212> TYPE: PRT
<213> ORGANISM: Saccharomyces cerevisiae

<400> SEQUENCE: 1

Met Ser Glu Ala Thr Leu Leu Ser Tyr Thr Lys Lys Leu Leu Ala Ser
1               5                   10                  15

Pro Pro Gln Leu Ser Ser Thr Asp Leu His Asp Ala Leu Leu Val Ile
            20                  25                  30

Leu Ser Leu Leu Gln Lys Cys Asp Thr Asn Ser Asp Glu Ser Leu Ser
        35                  40                  45

Ile Tyr Thr Lys Val Ser Ser Phe Leu Thr Ala Leu Arg Val Thr Lys
50                  55                  60

Leu Asp His Lys Ala Glu Tyr Ile Ala Glu Ala Ala Lys Ala Val Leu
65                  70                  75                  80

Arg His Ser Asp Leu Val Asp Leu Pro Leu Pro Lys Lys Asp Glu Leu
                85                  90                  95

His Pro Glu Asp Gly Pro Val Ile Leu Asp Ile Val Gly Thr Gly Gly
            100                 105                 110

Asp Gly Gln Asn Thr Phe Asn Val Ser Thr Ser Ala Ala Ile Val Ala
        115                 120                 125

Ser Gly Ile Gln Gly Leu Lys Ile Cys Lys His Gly Gly Lys Ala Ser
    130                 135                 140

Thr Ser Asn Ser Gly Ala Gly Asp Leu Ile Gly Thr Leu Gly Cys Asp
145                 150                 155                 160

Met Phe Lys Val Asn Ser Ser Thr Val Pro Lys Leu Trp Pro Asp Asn
                165                 170                 175

Thr Phe Met Phe Leu Leu Ala Pro Phe Phe His His Gly Met Gly His
            180                 185                 190

Val Ser Lys Ile Arg Lys Phe Leu Gly Ile Pro Thr Val Phe Asn Val
        195                 200                 205

Leu Gly Pro Leu Leu His Pro Val Ser His Val Asn Lys Arg Ile Leu
    210                 215                 220

Gly Val Tyr Ser Lys Glu Leu Ala Pro Glu Tyr Ala Lys Ala Ala Ala
225                 230                 235                 240

Leu Val Tyr Pro Gly Ser Glu Thr Phe Ile Val Trp Gly His Val Gly
                245                 250                 255

Leu Asp Glu Val Ser Pro Ile Gly Lys Thr Thr Val Trp His Ile Asp
            260                 265                 270
```

```
Pro Thr Ser Ser Glu Leu Lys Leu Lys Thr Phe Gln Leu Glu Pro Ser
        275                 280                 285

Met Phe Gly Leu Glu Glu His Glu Leu Ser Lys Cys Ala Ser Tyr Gly
        290                 295                 300

Pro Lys Glu Asn Ala Arg Ile Leu Lys Glu Val Leu Ser Gly Lys
305                 310                 315                 320

Tyr His Leu Gly Asp Asn Asn Pro Ile Tyr Asp Tyr Ile Leu Met Asn
                325                 330                 335

Thr Ala Val Leu Tyr Cys Leu Ser Gln Gly His Gln Asn Trp Lys Glu
                340                 345                 350

Gly Ile Ile Lys Ala Glu Glu Ser Ile His Ser Gly Asn Ala Leu Arg
                355                 360                 365

Ser Leu Glu His Phe Ile Asp Ser Val Ser Ser Leu
                370                 375                 380

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
cagaattcca ccgcgggctt attc                                          24

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
gagaattcgt agatatctta atctcctaga ttgggtttc                          39

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
atcatggctg acattctgct gctc                                          24

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
cactgcagtt accctcgtgc cgccagtg                                      28

<210> SEQ ID NO 6
<211> LENGTH: 1596
<212> TYPE: DNA
<213> ORGANISM: Escherichia coli

<400> SEQUENCE: 6
atggctgaca ttctgctgct cgataatatc gactctttta cgtacaacct ggcagatcag    60
```

```
ttgcgcagca atgggcataa cgtggtgatt taccgcaacc atattccggc gcaaaccta    120 attgaacgcc tggcgaccat gagcaatccg gtgctgatgc tttctcctgg ccccggtgtg    180
ccgagcgaag ccggttgtat gccggaactc ctcacccgct tgcgtggcaa gctgcccatt    240
attggcattt gcctcggaca tcaggcgatt gtcgaagctt acgggggcta tgtcggtcag    300
gcgggcgaaa ttctccacgg taaagcctcc agcattgaac atgacggtca ggcgatgttt    360
gccggattaa caaacccgct gccggtggcg cgttatcact cgctggttgg cagtaacatt    420
ccggccggtt taaccatcaa cgcccatttt aatggcatgg tgatggcagt acgtcacgat    480
gcggatcgcg tttgtggatt ccagttccat ccggaatcca ttctcaccac ccagggcgct    540
cgcctgctgg aacaaacgct ggcctgggcg cagcagaaac tagagccagc caacacgctg    600
caaccgattc tggaaaaact gtatcaggcg cagacgctta gccaacaaga aagccaccag    660
ctgttttcag cggtggtgcg tggcgagctg aagccggaac aactggcggc ggcgctggtg    720
agcatgaaaa ttcgcggtga gcacccgaac gagatcgccg gggcagcaac cgcgctactg    780
gaaaacgcag cgccgttccc gcgcccggat tatctgtttg ctgatatcgt cggtactggc    840
ggtgacggca gcaacagtat caatatttct accgccagtg cgtttgtcgc gcggcctgt     900 gggctgaaag tggcgaaaca cggcaaccgt agcgtctcca gtaaatctgg ttcgtccgat    960
ctgctggcgg cgttcggtat taatcttgat atgaacgccg ataaatcgcg ccaggcgctg   1020
gatgagttag gtgtatgttt cctctttgcg ccgaagtatc acaccggatt ccgccacgcg   1080
atgccggttc gccagcaact gaaaacccgc accctgttca atgtgctggg gccattgatt   1140
aacccggcgc atccgccgct ggcgttaatt ggtgtttata gtccggaact ggtgctgccg   1200
attgccgaaa ccttgcgcgt gctggggtat caacgcgcgg cggtggtgca cagcggcggg   1260
atggatgaag tttcattaca cgcgccgaca atcgttgccg aactgcatga cggcgaaatt   1320
aaaagctatc agctcaccgc agaagacttt ggcctgacac cctaccacca ggagcaactg   1380
gcaggcggaa caccggaaga aaaccgtgac attttaacac gtttgttaca aggtaaaggc   1440
gacgccgccc atgaagcagc cgtcgctgcg aacgtcgcca tgttaatgcg cctgcatggc   1500
catgaagatc tgcaagccaa tgcgcaaacc gttcttgagg tactgcgcag tggttccgct   1560
tacgacagag tcaccgcact ggcggcacga gggtaa                              1596
```

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
atcatgtccg aggcgacttt gctatc                                         26

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
gtctgcagct acaaggagct cacactatct ataaag                              36

<210> SEQ ID NO 9

```
<211> LENGTH: 1143
<212> TYPE: DNA
<213> ORGANISM: Saccharomyces cerevisiae

<400> SEQUENCE: 9
atgtccgagg cgactttgct atcttacacc aagaaattat tggcttctcc gccgcaattg        60
agtagcacag acctacacga tgcgttgctg gttatattaa gtcttttgca aaaatgtgat       120
acaaatagcg atgagagtct ttccatctat accaaagttt cgagttttct cacggccttg       180
agagttacta aacttgatca caaggctgaa tacattgcgg aagctgcaaa ggctgtgctc       240
agacattccg accttgttga tctaccttta cccaagaagg acgaattaca cccggaagat       300
ggaccagtaa tcttagatat tgtaggtact ggtggtgacg gacagaatac tttttaatgtt      360 tccacgtctg ctgctatcgt tgcctccgga attcagggcc taaaaatttg taagcacggt       420
ggtaaagctt ctacatccaa tagtggagct ggtgacctaa ttggaacttt aggctgtgac       480
atgttcaagg ttaattcatc gacagtgccc aaactttggc ctgataatac gttcatgttt       540
ctacttgctc cttttttttca tcatggaatg ggccacgttt ctaagatacg caaatttctt     600
ggaattccga ctgttttcaa cgtactggga ccacttctac atccagttag ccacgtaaac      660
aagagaatat tgggcgttta ctcaaaggaa cttgcgcctg aatatgccaa ggcagccgct      720
ttggtatatc caggaagcga aactttttata gtttggggac atgttgggtt agacgaagta    780
tcacctatag gcaaaactac tgtctggcat attgatccga catcgtccga acttaaattg      840
aagaccttcc aattagaacc ttctatgttt ggtttagaag aacacgagtt gtcgaagtgt      900
gcttcatacg gccctaaaga gaatgcgaga attctaaaag aagaagtctt gtccggcaag      960
taccaccttg gcgacaataa tcctatttat gactacatct tgatgaacac cgccgtgtta     1020
tattgtttaa gccaaggtca ccagaactgg aaggaaggga tcattaaggc agaagaaagc    1080
atacattctg gtaatgcatt acgttcttta gaacacttta tagatagtgt gagctccttg    1140
tag                                                                   1143

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
caggtaccca ccgcgggctt attc                                              24

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gtactagtct acaaggagct cacactatct ataaag                                 36

<210> SEQ ID NO 12
<211> LENGTH: 70
<212> TYPE: DNA
<213> ORGANISM: Artificial Sequence
<220> FEATURE:
<223> OTHER INFORMATION: primer

<400> SEQUENCE: 12
```
tcgcgaacaa ctggaacaag ccgaatgggt ggatggacgc gtcaccaccg ataggcctag    60
gatgcatatg                                                           70

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
acaggatctc ttcactttcg ccgtagcggc ttttcagcga ctgaatattg ccaaaacagc    60
caagctttac                                                           70

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
atgatgtacc acattcccgg cgtgttatcg ccacaggacg tcgctcgttt tcgcgaacaa    60
ctggaacaag                                                           70

<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
tcagatctcc gaccattccc gcagcagatt atgataaaga ttaagcagcg acaggatctc    60
ttcactttcg                                                           70

<210> SEQ ID NO 16
<211> LENGTH: 2824
<212> TYPE: DNA
<213> ORGANISM: Artificial Sequence
<220> FEATURE:
<223> OTHER INFORMATION: Synthetic

<400> SEQUENCE: 16
tcagatctcc gaccattccc gcagcagatt atgataaaga ttaagcagcg acaggatctc    60
ttcactttcg ccgtagcggc ttttcagcga ctgaatattg ccaaaacagc caagctttac   120
cgttcgtata gcatacatta tacgaagtta tctgccctga accgacgacc gggtcgaatt   180
tgctttcgaa tttctgccat tcatccgctt attatcactt attcaggcgt agcaaccagg   240
cgtttaaggg caccaataac tgccttaaaa aaattacgcc ccgccctgcc actcatcgca   300
gtactgttgt aattcattaa gcattctgcc gacatggaag ccatcacaaa cggcatgatg   360
aacctgaatc gccagcggca tcagcaccct gtcgccttgc gtataatatt tgcccatggt   420
gaaaacgggg gcgaagaagt tgtccatatt ggccacgttt aaatcaaaac tggtgaaact   480
cacccaggga ttggctgaga cgaaaaacat attctcaata aacccttttag ggaaataggc   540 caggttttca ccgtaacacg ccacatcttg cgaatatatg tgtagaaact gccgaaatc   600 gtcgtggtat tcactccaga gcgatgaaaa cgtttcagtt tgctcatgga aaacggtgta   660

```
acaagggtga acactatccc atatcaccag ctcaccgtct ttcattgcca tacggaattc    720
cggatgagca ttcatcaggc gggcaagaat gtgaataaag gccggataaa acttgtgctt    780
atttttcttt acggtcttta aaaggccgt aatatccagc tgaacggtct ggttataggt    840
acattgagca actgactgaa atgcctcaaa atgttcttta cgatgccatt gggatatatc    900
aacggtggta tatccagtga tttttttctc cattttagct tccttagctc ctgaaaatct    960
cgataactca aaaatacgc ccggtagtga tcttatttca ttatggtgaa agttggaacc   1020
tcttacgtgc cgatcaacgt ctcatttttcg ccaaaagttg gcccagggct tcccggtatc   1080
aacagggaca ccaggattta tttattctgc gaagtgatct tccgtcacag gtatttattc   1140
ggcgcaaagt gcgtcgggtg atgcataact tcgtatagca tacattatac gaacggtacc   1200
catcagatcc ctcgagctac aaggagctca cactatctat aaagtgttct aaagaacgta   1260
atgcattacc agaatgtatg cttttcttctg ccttaatgat cccttccttc cagttctggt   1320
gaccttggct taaacaatat aacacggcgg tgttcatcaa gatgtagtca taaataggat   1380
tattgtcgcc aaggtggtac ttgccggaca agacttcttc ttttagaatt ctcgcattct   1440
ctttagggcc gtatgaagca cacttcgaca actcgtgttc ttctaaacca aacatagaag   1500
gttctaattg gaaggtcttc aatttaagtt cggacgatgt cggatcaata tgccagacag   1560
tagttttgcc tataggtgat acttcgtcta acccaacatg tccccaaact ataaagtttt   1620
cgcttcctgg atataccaaa gcggctgcct tggcatattc aggcgcaagt tcctttgagt   1680
aaacgcccaa tattctcttg tttacgtggc taactggatg tagaagtggt cccagtacgt   1740
tgaaaacagt cggaattcca agaaatttgc gtatcttaga aacgtggccc attccatgat   1800
gaaaaaaagg agcaagtaga acatgaacg tattatcagg ccaaagtttg ggcactgtcg   1860
atgaattaac cttgaacatg tcacagccta aagttccaat taggtcacca gctccactat   1920
tggatgtaga agctttacca ccgtgcttac aaatttttag gccctgaatt ccggaggcaa   1980
cgatagcagc agacgtggaa acattaaaag tattctgtcc gtcaccacca gtacctacaa   2040
tatctaagat tactggtcca tcttccgggt gtaattcgtc cttcttgggt aaaggtagat   2100
caacaaggtc ggaatgtctg agcacagcct ttgcagcttc cgcaatgtat tcagccttgt   2160
gatcaagttt agtaactctc aaggccgtga gaaaactcga aactttggta tagatggaaa   2220
gactctcatc gctatttgta tcacattttt gcaaaagact taatataacc agcaacgcat   2280
cgtgtaggtc tgtgctactc aattgcggcg gagaagccaa taatttcttg gtgtaagata   2340
gcaaagtcgc ctcggacatg atatcttaat ctcctagatt gggtttcact caaggttat   2400 gttccacgca ggcgcccgcg acggcaggat tggtgagtgt gtaccaacct caacctggtg   2460
tcagcaacca ttctggcact cagcccctc gagtgcaaga aaaaggtac ttgagatcat    2520 aaatctccag ctcaccagcg tgcctgcaca tgtcattatt ttctctcctg gttggcagca   2580
tcggatcaga agctcccgac acagtcaatt tcgtcgcatt ccctgccatt cctggtcatt   2640
ccatgtaatg gaataagccc gcggtggtcg acgtcccatg tgcaggtgct ctgcaggcgg   2700
ccgccatatg catcctaggc ctatcggtgg tgacgcgtcc atccacccat tcggcttgtt   2760
ccagttgttc gcgaaaacga gcgacgtcct gtggcgataa cacgccggga atgtggtaca   2820
tcat                                                                2824
```

<210> SEQ ID NO 17
<211> LENGTH: 25
<212> TYPE: DNA
<213> ORGANISM: Artificial Sequence

```
<220> FEATURE:
<223> OTHER INFORMATION: primer

<400> SEQUENCE: 17
cctcaatcaa caagagcggc taccg                                              25

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
gcaccgcact cttcacattc atccag                                             26

<210> SEQ ID NO 19
<211> LENGTH: 383
<212> TYPE: PRT
<213> ORGANISM: saccharomyces kudriavzevii

<400> SEQUENCE: 19
```

Met Leu Glu Ala Ala Leu Leu Ser Leu Thr Lys Lys Leu Leu Val Ser
1               5                   10                  15

Pro Pro Lys Leu Thr Ser Thr Asp Leu His Asp Ala Leu Leu Val Ile
            20                  25                  30

Leu Asp Leu Leu Arg Lys Cys Asp Met Asn Asp Asp Glu Ser Leu Ser
        35                  40                  45

Ile Tyr Thr Lys Val Ser Ser Phe Leu Thr Ala Leu Arg Val Thr Gln
50                  55                  60

Leu Asp His Lys Ala Glu Tyr Ile Ala Glu Ala Ala Lys Ala Val Leu
65                  70                  75                  80

Arg His Ser Asp Leu Val Asp Leu Pro Ser Pro Ala Lys Ser Glu Ser
                85                  90                  95

His Pro Glu Lys Gly Pro Ile Thr Leu Asp Ile Val Gly Thr Gly Gly
            100                 105                 110

Asp Gly Gln Asn Thr Phe Asn Val Ser Thr Ser Ala Ala Ile Val Ala
        115                 120                 125

Ala Gly Ile Pro Gly Leu Lys Ile Cys Lys His Gly Gly Lys Ala Ser
130                 135                 140

Thr Ser Asn Ser Gly Ala Gly Asp Leu Ile Gly Thr Leu Gly Cys Asp
145                 150                 155                 160

Ile Ser Lys Val Asn Ser Ser Thr Val Pro Gly Leu Trp Pro Asp Asn
                165                 170                 175

Thr Phe Leu Phe Leu Leu Ala Pro Phe Phe His His Gly Met Ser His
            180                 185                 190

Val Ser Lys Ile Arg Lys Leu Leu Gly Ile Pro Thr Ile Phe Asn Val
        195                 200                 205

Leu Gly Pro Leu Leu His Pro Ile Ser His Val Asn Lys Arg Ile Leu
210                 215                 220

Gly Val Tyr Ser Lys Glu Leu Ala Pro Glu Tyr Ala Lys Ala Ala Ala
225                 230                 235                 240

Leu Val Tyr Pro Glu Ser Glu Thr Phe Ile Val Trp Gly His Val Gly
                245                 250                 255

Leu Asp Glu Val Ser Pro Ile Gly Lys Thr Thr Val Trp His Ile Asp
            260                 265                 270

Pro Leu Ser Ser Ala His Ser Asn Asp Gln Leu Lys Thr Phe Gln Leu

```
                275                 280                 285
Glu Pro Ser Met Phe Gly Leu Lys Glu His Glu Leu Ser Glu Cys Ala
290                 295                 300

Ser Tyr Gly Pro Lys Glu Asn Ala Arg Ile Leu Arg Glu Glu Ile Leu
305                 310                 315                 320

Ser Gly Lys Tyr His Leu Gly Asp Asn Asn Ala Ile Tyr Asp Tyr Ile
                325                 330                 335

Leu Met Asn Thr Ala Val Leu Tyr Cys Leu Ser Gln Gly His Gln Asn
                340                 345                 350

Trp Lys Glu Gly Ile Ile Lys Ala Glu Glu Ser Ile Gln Ser Gly Asn
                355                 360                 365

Ala Leu His Ser Leu Glu His Phe Ile Thr Ser Val Asn Ser Leu
370                 375                 380
```

<210> SEQ ID NO 20
<211> LENGTH: 384
<212> TYPE: PRT
<213> ORGANISM: saccharomyces arboricola

<400> SEQUENCE: 20

```
Met Ser Glu Ala Thr Leu Leu Ser Phe Thr Lys Leu Leu Ala Ser
1               5                   10                  15

Pro Pro Gln Leu Ser Ser Thr Asp Leu His Asp Ala Leu Leu Val Ile
                20                  25                  30

Leu Asp Leu Leu Gln Lys Cys Asp Thr Asn Asn Asp Glu Ser Leu Ser
                35                  40                  45

Ile Tyr Thr Lys Val Ser Ser Phe Leu Thr Ala Leu Arg Val Thr Lys
50                  55                  60

Leu Asp His Lys Ala Glu Tyr Ile Ala Glu Ala Ala Lys Ala Val Leu
65                  70                  75                  80

Lys Tyr Ser Asp Leu Val Asp Leu Pro Leu Pro Ala Asn Ser Lys Ser
                85                  90                  95

Arg Ile Glu Ser Glu Pro Val Thr Leu Asp Ile Val Gly Thr Gly Gly
                100                 105                 110

Asp Gly Gln Asn Thr Phe Asn Val Ser Thr Ser Ala Ala Ile Val Ala
                115                 120                 125

Ser Gly Ile Pro Gly Leu Lys Ile Cys Lys His Gly Gly Lys Ala Ser
130                 135                 140

Thr Ser Asn Ser Gly Ala Gly Asp Leu Ile Gly Thr Leu Gly Cys Asp
145                 150                 155                 160

Val Ser Lys Val Asn Ser Ser Thr Val Ala Ser Leu Trp Pro Asp Asn
                165                 170                 175

Thr Phe Leu Phe Leu Leu Ala Pro Phe Phe His His Gly Met Gly His
                180                 185                 190

Val Ala Lys Ile Arg Lys Leu Leu Gly Ile Pro Thr Ile Phe Asn Val
                195                 200                 205

Leu Gly Pro Leu Leu His Pro Val Ser His Val Lys Lys Arg Val Leu
                210                 215                 220

Gly Val Tyr Ser Lys Glu Leu Ala Pro Glu Tyr Ala Lys Ala Ala
225                 230                 235                 240

Leu Val Tyr Pro Glu Ser Glu Thr Phe Ile Val Trp Gly His Val Gly
                245                 250                 255

Leu Asp Glu Val Ser Pro Ile Gly Lys Thr Thr Val Trp His Ile Asn
                260                 265                 270
```

```
Pro Thr Leu Ser Ser His Ser Asn Glu Thr Gln Met Lys Thr Phe Gln
        275             280             285

Leu Glu Pro Ser Met Phe Gly Leu Glu Glu His Glu Leu Ser Glu Cys
    290             295             300

Ala Ser Phe Gly Pro Gln Glu Asn Ala Arg Ile Leu Lys Glu Asp Ile
305             310             315             320

Leu Ser Gly Lys Tyr His Leu Gly Asp Ser Asn Ala Val Tyr Asp Tyr
            325             330             335

Ile Leu Met Asn Thr Ala Val Leu Tyr Cys Leu Ser Gln Gly His Gln
            340             345             350

Asn Trp Lys Glu Gly Ile Ile Lys Ala Glu Glu Ser Ile Gln Ser Gly
        355             360             365

Asn Ala Leu Arg Ser Leu Glu His Phe Ile Ala Gly Val Ser Ser Leu
    370             375             380
```

MICROORGANISMS HAVING L-TRYPTOPHAN PRODUCTIVITY AND A METHOD FOR PRODUCTION OF L-TRYPTOPHAN USING SAME

CROSS REFERENCE TO RELATED APPLICATIONS

This application is a National Stage Entry of International Application No. PCT/KR2014/003327 filed on Apr. 16, 2014, and claims the benefit of Korean Application Nos. 10-2013-0041547, filed on Apr. 16, 2013 and 10-2014-0045650, filed on Apr. 16, 2014, which are hereby incorporated by reference in their entirety for all purposes as if fully set forth herein.

TECHNICAL FIELD

The present invention relates to a recombinant microorganism having enhanced L-tryptophan productivity and a method of producing L-tryptophan using the microorganism.

Incorporated by reference herein in its entirety is the Sequence Listing entitled "Sequence list.txt", created Oct. 6, 2015, size of 15 kilobytes.

BACKGROUND ART

L-tryptophan, a kind of essential amino acid, has been widely used as a feed and food additive. L-tryptophan is generally produced by fermentation using microorganisms of the genus *Corynebacterium*, *Bacillus* or *Escherichia*, and variant thereof. L-tryptophan is biosynthesized from chorismic acid which is a common intermediate for the synthesis of aromatic amino acids. Specifically, L-tryptophan is biosynthesized by the action of five enzymes, which are synthesized by the tryptophan operon trpEDCBA, on chorismic acid produced through the common shikimic acid pathway that starts from phosphoenolpyruvate and D-erythrose-4-phosphate. First, anthranilate synthase (TrpE-TrpD complex) acts on chorismic acid to synthesize anthranilic acid, then anthranilate phosphoribosyltransferase (TrpD) acts on it to synthesize N-(5'-phosphoribosyl)-anthranilate. Then, phosphoribosylanthranilate isomerase (TrpC) and indole-3-glycerol phosphate synthase (TrpC) act on the N-(5'-phosphoribosyl)-anthranilate to synthesize indole-3-glycerol-phosphate, then tryptophan synthase (TrpB-TrpA complex) acts on it to synthesize L-tryptophan (FIG. 1; Bonggaerts et al., *Metab Eng*, 3, 289-300, 2001).

In *E. coli*, a protein encoded by a complex of the trpE and trpD genes forms anthranilate synthase to synthesize anthranilic acid. The synthesized anthranilic acid reacts with 5-phosphoribosyl 1-pyrophosphate (PRPP) by anthranilate phosphoribosyltransferase encoded by the trpD gene, thereby synthesizing N-(5'-phosphoribosyl)-anthranilate.

Herein, the protein encoded by the trpD gene acts as anthranilate synthase in combination with the protein encoded by the trpE gene or acts alone as anthranilate phosphoribosyltransferase, and a wild-type *E. coli* strain maintains the balance of such two actions.

In a wild-type *E. coli* strain, the concentration of PRPP that is used as a cofactor in intracellular tryptophan biosynthesis is about 180 μM (Bennett et al., *Nat Chem Biol*, 5, 595-599, 2009). In an L-tryptophan-producing strain with enhanced biosynthesis of anthranilic acid, the extracellularly accumulated concentration of anthranilic acid is at the maximum value, whereas the intracellular concentration of PRPP is greatly lower than the concentration of anthranilic acid. Low PRPP concentration acts as a limiting factor in the production of N-(5'-phosphoribosyl)-anthranilate to reduce the overall synthesis rate of L-tryptophan and increase the intracellular and extracellular accumulation of anthranilic acid. Thus, the use of an anthranilate phosphoribosyltransferase having higher affinity for PRPP makes it possible to prevent the intracellular and extracellular accumulation of anthranilic acid and to increase the biosynthesis rate of L-tryptophan.

Among previous reports on improvement in L-tryptophan-producing strains, a technology of enhancing the biosynthesis pathway while maintaining the balance of anthranilate synthase and anthranilate phosphoribosyltransferase activities has not yet been reported.

According to studies, the $K_m$ value of *E. coli* for PRPP is 50, whereas the $K_m$ value of yeast for PRPP is about 22.4±2.6 (Hommel et al., *Eur J Biochem*, 180, 33-40, 1989). Thus, the affinity of yeast anthranilate phosphoribosyltransferase for PRPP is higher than that of *E. coli* anthranilate phosphoribosyltransferase. Thus, it is expected that the use of yeast anthranilate phosphoribosyltransferase will have greater effects on the prevention of the intracellular and extracellular accumulation of anthranilic acid and an increase in the biosynthesis of L-tryptophan in microorganisms with enhanced L-tryptophan biosynthesis pathways.

During an attempt to enhance the chorismic acid biosynthesis pathway and trp operon pathway in *E. coli* in order to produce a large amount of industrially useful L-tryptophan, the present inventors have found that, as the above two pathways are enhanced, anthranilic acid is accumulated intracellularly and extracellularly, and for this reason, abnormal culture appears. Accordingly, the present inventors have continued to study under the expectation that enhancement of the expression of anthranilate phosphoribosyltransferase in microorganisms having an enhanced L-tryptophan biosynthesis pathway can prevent the intracellular and extracellular accumulation of anthranilic acid and increase the biosynthesis of L-tryptophan, thereby completing the present invention.

DISCLOSURE

Technical Problem

Therefore, it is an object of the present invention is to provide a microorganism having enhanced L-tryptophan productivity, which has been modified to express yeast anthranilate phosphoribosyltransferase (trp4).

Another object of the present invention is to provide a method of producing L-tryptophan using the above microorganism.

Technical Solution

In order to accomplish the above objects, the present invention provides a microorganism of the genus *Escherichia* having enhanced L-tryptophan productivity, which has been modified to express yeast anthranilate phosphoribosyltransferase.

The present invention also provides a method for producing L-tryptophan, the method comprising the steps of: culturing the microorganism of the genus *Escherichia*; and recovering L-tryptophan from the culture.

Advantageous Effects

The microorganism according to the present invention can produce L-tryptophan in high yield, and thus can be advantageously used in the pharmaceutical industry and the feed industry, particularly in the animal feed field.

DESCRIPTION OF DRAWINGS

FIG. 2 shows the amino acid sequence homology of yeast anthranilate phosphoribosyltransferases (Seq ID Nos. 1, 19 and 20).

FIG. 3 shows pCL-P$_{CJ1}$-trpD and pCL-P$_{CJ1}$-trp4 vectors.

MODE FOR INVENTION

Figure 1:
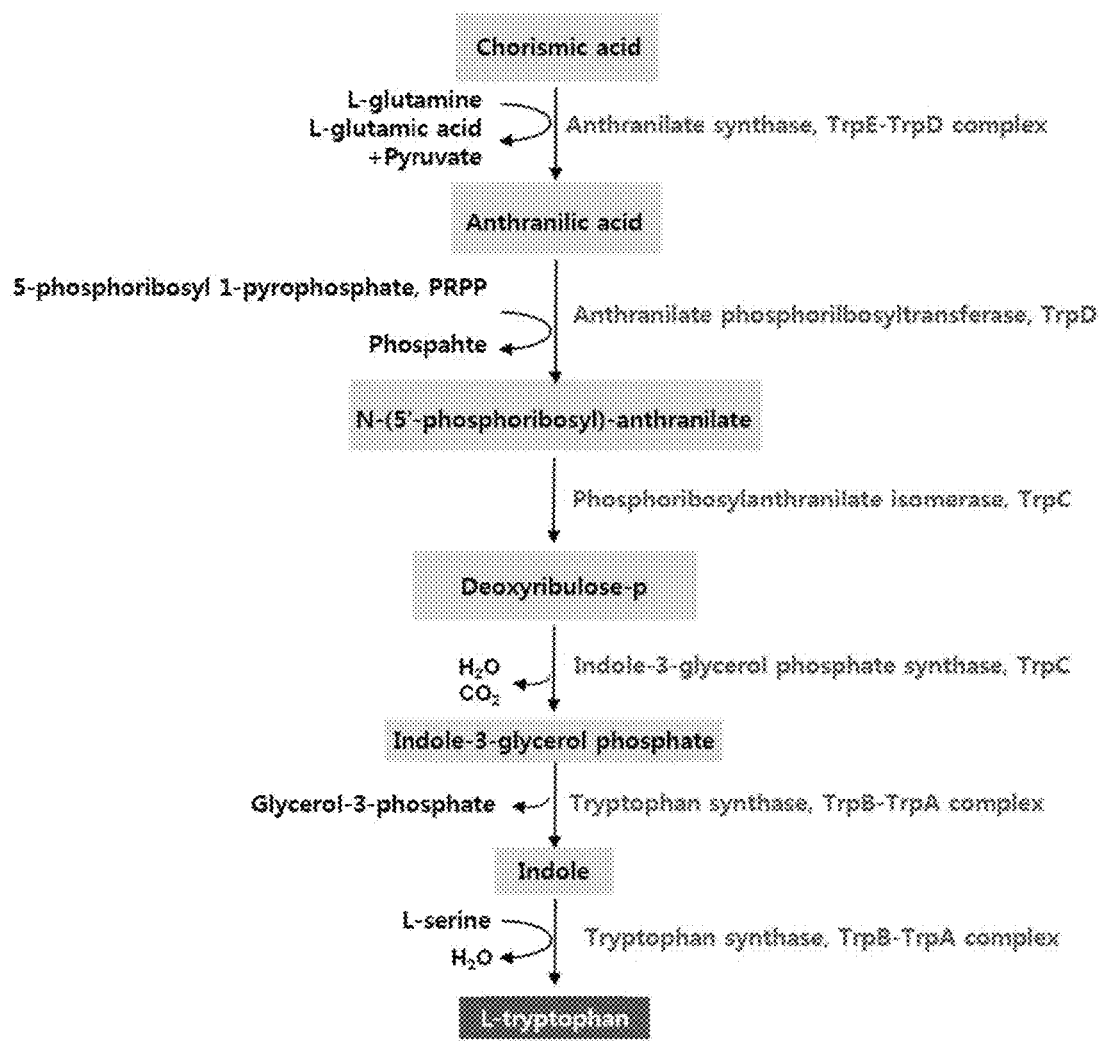
FIG. 1 is a schematic view showing the L-tryptophan biosynthesis pathway in *E. coli* and proteins that are involved therein.
Figure 4:
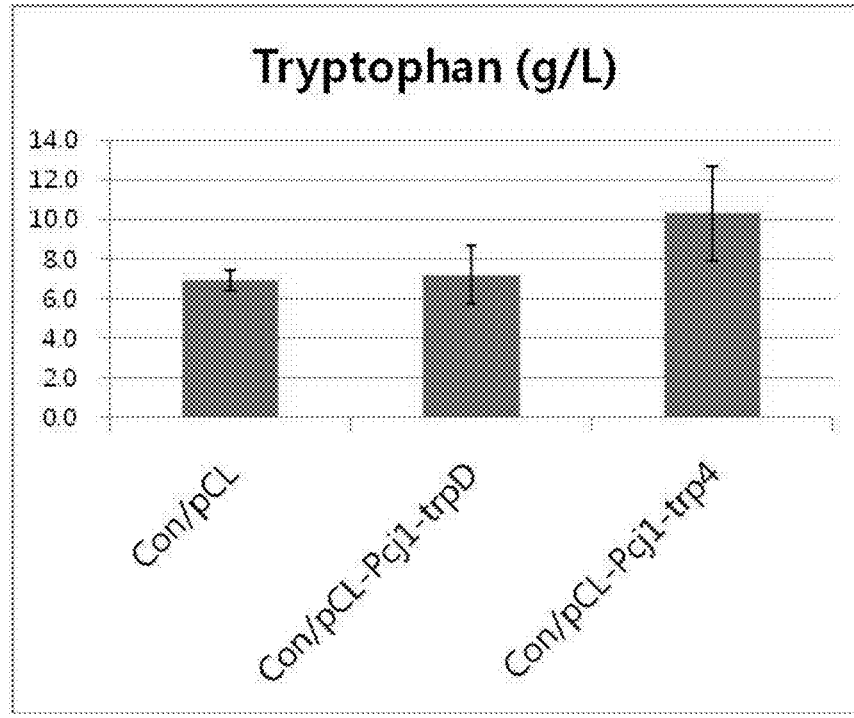
FIG. 4 shows a comparison of L-tryptophan productivity at hours of fermentation between an L-tryptophan-producing parent strain and a strain transformed with the vector pCL-P$_{CJ1}$-trpD or pCL-P$_{CJ1}$-trp4.
Figure 5:
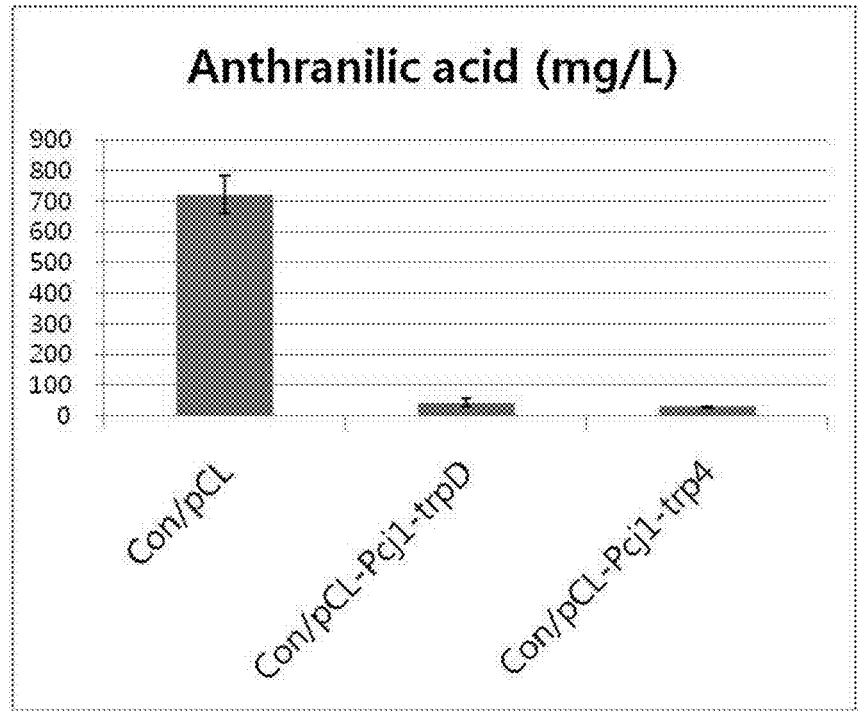
FIG. 5 shows a comparison of the accumulation of the tryptophan precursor anthranilic acid after fermentation between an L-tryptophan-producing parent strain and a strain transformed with the vector pCL-P$_{CJ1}$-trpD or pCL-P$_{CJ1}$-trp4.
Figure 6:
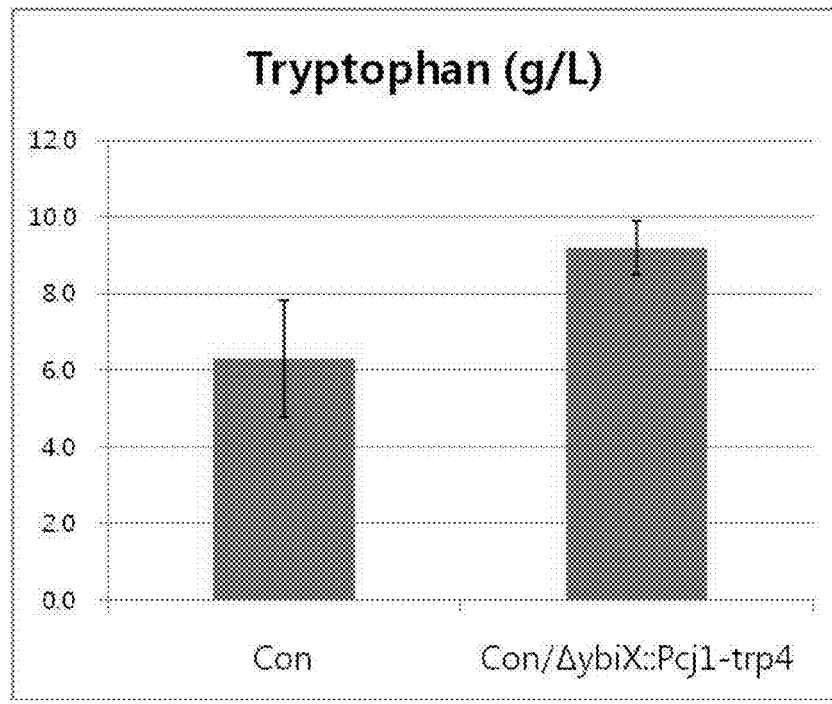
FIG. 6 shows a comparison of L-tryptophan productivity at hours of fermentation between an L-tryptophan-producing parent strain and strains having a trp4 gene expression cassette inserted in the genome.
Figure 7:
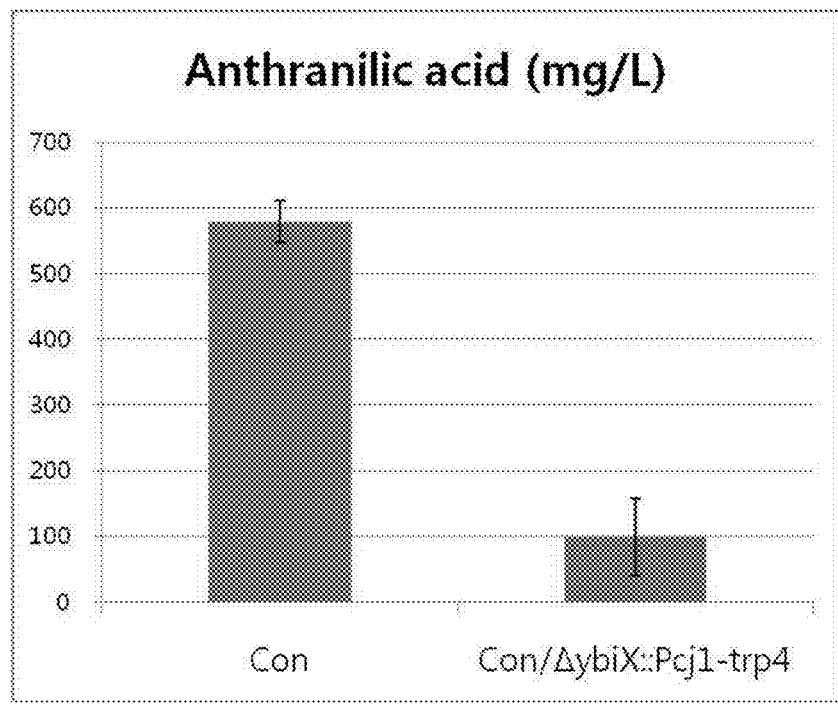
FIG. 7 shows a comparison of the accumulation of anthranilic acid after fermentation between an L-tryptophan-producing parent strain and strains having a trp4 gene expression cassette inserted in the genome.

Hereinafter, the present invention will be described in detail.

The present invention provides a microorganism of the genus *Escherichia* having enhanced L-tryptophan productivity, which has been modified to express yeast anthranilate phosphoribosyltransferase.

Anthranilate phosphoribosyltransferase is an enzyme that synthesizes phosphoribosyl anthranilate using anthranilic acid and PRPP. In strains having enhanced L-tryptophan productivity, the synthesis of chorismic acid is increased through an enhanced shikimic acid pathway, resulting in an increase of anthranilic acid. The increased anthranilic acid is accumulated intracellularly and extracellularly to interfere with the normal physiological activity of the cells to thereby inhibit the production of L-tryptophan.

Thus, the present invention is intended to prevent the intracellular and extracellular accumulation of anthranilic acid by enhancement of the expression of anthranilate phosphoribosyltransferase to thereby enhance the biosynthesis of L-tryptophan.

Herein, the present invention is intended to further increase the synthesis rate of phosphoribosyl anthranilate by using yeast anthranilate phosphoribosyltransferase having a higher affinity for PRPP compared to an anthranilate phosphoribosyltransferase which is encoded by trpD gene in *E. coli*.

The anthranilate phosphoribosyltransferase that is used in the present invention is derived from yeast, and it may be seen that anthranilate phosphoribosyltransferases from various species of yeast have an amino acid sequence homology of 87% or more (FIG. 2) (Seq ID Nos. 1, 19 and 20). Specifically, the anthranilate phosphoribosyltransferase that is used in the present invention has an amino acid sequence represented by SEQ ID NO: 1. However, the anthranilate phosphoribosyltransferase that is used in the present invention is not limited thereto, because the amino acid sequence of an enzyme showing anthranilate phosphoribosyltransferase activity may differ depending on the species or strain of microorganisms. Specifically, the anthranilate phosphoribosyltransferase that is used in the present invention may be a mutant or artificial variant encoding a polypeptide having an amino acid sequence comprising a substitution, deletion, insertion or addition of one or several amino acids at one or more positions of the amino acid sequence of SEQ ID NO: 1, or a silent mutation causing a change into a similar amino acid, as long as the activity of the anthranilate phosphoribosyltransferase can be maintained or enhanced. As used herein, the term "several amino acids" means 2-20 amino acids, preferably 2-10 amino acids, and more preferably 2-5 amino acids, depending on the type or positions of amino acid residues in the three-dimensional structure of the protein. Furthermore, the substitutions, deletions, insertions, additions, or inversions of amino acids may include naturally occurring mutants or artificial variants, based on individual differences and/or species differences of the microorganism having the yeast anthranilate phosphoribosyltransferase.

In the present invention, enhancement of the yeast anthranilate phosphoribosyltransferase may be achieved either by transformation with a vector comprising a polynucleotide encoding the yeast anthranilate phosphoribosyltransferase or by insertion of the polynucleotide into the chromosome.

The polynucleotide encoding the yeast anthranilate phosphoribosyltransferase is represented by SEQ ID NO: 9. The polynucleotide may be transformed into a host cell. For this, the polynucleotide may be substituted with a codon favored by the host cell, or the N terminus or C terminus thereof may be extended or eliminated, or the start codon thereof may be modified to control expression level. Thus, the polynucleotide of the present invention may have a polynucleotide sequence encoding a protein having a homology of at least 80%, specifically at least 90%, more specifically at least 95%, particularly specifically at least 97%, to the amino acid sequence of SEQ ID NO: 1, as long as it may maintain or enhance the activity of the yeast anthranilate phosphoribosyltransferase of the variant of the present invention. Most specifically, the polynucleotide of the present invention may have a polynucleotide sequence represented by SEQ ID NO: 9.

As used herein, the term "homology" refers to the identity between two amino acid sequences. The homology can be determined using methods well known to those skilled in the art, for example, BLAST 2.0 which calculates parameters such as score, identity or similarity.

In addition, the polynucleotide sequence according to the present invention may be a variant encoding yeast anthranilate phosphoribosyltransferase, which may hybridize to the polynucleotide sequence of SEQ ID NO: 9 or a probe derived from the polynucleotide sequence under stringent conditions and which normally functions.

As used herein, the term "stringent conditions" means conditions which permit specific hybridization between polynucleotides. Such stringent conditions are described in detail in Molecular Cloning, A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York, which describe, for example, hybridization in a hybridization buffer (3.5× SSC, 0.02% Ficoll, 0.02% polyvinylpyrrolidone, 0.02% bovine serum albumin, 2.5 mM NaH$_2$PO$_4$ (pH 7), 0.5% SDS, 2 mM EDTA) at 65° C. Herein, SSC is 0.15 M sodium chloride/0.15 M sodium citrate (pH 7). After hybridization, the membrane having DNA transferred thereto is washed with 2×SSC at room temperature, and then washed with 0.1-0.5×SSC/0.1×SDS at a temperature of 68° C.

The vector that is used in the present invention is not specifically limited and may be any vector known in the art, as long as it can replicate in a host. Examples of the vectors that are commonly used include natural or recombinant plasmids, cosmids, viruses, and bacteriophages. For example, the phage vector or cosmid vector that is used in the present invention may be pWE15, M13, λMBL3, λMBL4, λIXII, λASHII, λAPII, λt10, λt11, Charon4A, Charon21A or the like, and the plasmid vector that is used in the present invention may be pBR type, pUC type, pBluescriptII type, pGEM type, pTZ type, pCL type, pET type or the like. Most preferably, a pACYC177, pCL or pCC1BAC vector may be used.

In addition, a new polynucleotide encoding a target protein may be inserted into a specific genetic locus in the chromosome through a DNA fragment comprising a polynucleotide for insertion into the bacterial chromosome. Insertion of the new polynucleotide into the chromosome may be achieved by any method known in the art, for example, by homologous recombination. The polynucleotide for insertion into the chromosome according to the present invention may further comprise a selection marker for confirming whether the polynucleotide was inserted into the chromosome, because it may be inserted into the chromosome by causing homologous recombination. The selection marker may be used to select transformed cells, that is, confirm whether the polynucleotide of interest was inserted. Thus, markers that impart selectable phenotypes such as drug resistance, auxotrophy, resistance to cytotoxic agents or the expression of surface proteins may be used in the present invention. In an environment treated with a selective agent, only the cells expressing the selection marker survive or show a different phenotype, and thus transformed cells can be selected.

As used herein, the term "transformation" means introducing a vector comprising a polynucleotide encoding a target protein into a host cell so as to be able to express a protein encoded by the polynucleotide in the host cell. The transformed polynucleotide may be inserted and located in the chromosome of the host cell or located outside the chromosome, as long as it can be expressed in the host cell. In addition, the polynucleotides include DNA and RNA, which encode the target protein. As long as the polynucleotide can be introduced in the host cell and expressed therein, it may be introduced in any form. For example, the polynucleotide can be introduced into the host cell in the form of an expression cassette which is a polynucleotide construct including all elements required for self-expression. The expression cassette generally includes a promoter which is operably linked to the open reading frame (hereinafter abbreviated as "ORF") of the gene, a transcription termination signal, a ribosome binding site, and a translation termination signal. The promoter that is used in the present invention is not specifically limited and may be any promoter known in the art, as long as it initiates the transcription of the target protein-encoding polynucleotide in a host cell. Specifically, T7 promoter, trc promoter, tac promoter, CJ1 promoter (Korean Patent No. 0620092), etc., may be used. Most specifically, trc promoter or CJ1 promoter may be used.

The expression cassette may be in the form of a self-replicable expression vector. In addition, the polynucleotide may be introduced into the host cell by itself and operably linked to the sequence necessary for expression in the host cell.

The microorganism of the present invention includes any prokaryotic microorganism, as long as it can produce L-tryptophan. For example, it may include a microorganism belonging to the genus *Escherichia*, the genus *Erwinia*, the genus *Serratia*, the genus *Providencia*, the genus *Corynebacterium* or the genus *Brevibacterium*. Specifically, the microorganism of the present invention is a microorganism belonging to the genus *Escherichia*. More specifically, it is *Escherichia coli*.

In order for the microorganism of the present invention to produce L-tryptophan, the activity of at least one enzyme selected from the group consisting of anthranilate synthase (trpE), phosphoglycerate dehydrogenase (serA), 3-deoxy-D-arabino-heptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB), in the microorganism, may further be enhanced, or the activity of chorismate mutase/prephenate dehydratase or chorismate mutase/prephenate dehydrogenase in the microorganism may further be attenuated. In addition, the microorganism of the present invention may be modified such that one or more of anthranilate synthase and phosphoglycerate dehydrogenase are released from the feedback inhibition by L-tryptophan and L-serine.

In a specific example of the present invention, *E. coli* was transformed with a vector comprising the gene (trp4) encoding the yeast anthranilate phosphoribosyltransferase represented by SEQ ID NO: 1, and the constructed strain was named CA04-2006, and deposited with the Korean Culture Center of Microorganisms (361-221, Honje 1-dong, Seodaemun-gu, Seoul, South Korea), an international depository authority, on Apr. 8, 2013 under the accession number KCCM11408P.

In addition, the present invention provides a method for producing L-tryptophan, comprising the steps of: culturing a microorganism of the genus *Escherichia* having L-tryptophan productivity, which has been modified to express a yeast anthranilate phosphoribosyltransferase having an amino acid sequence set forth in SEQ ID NO: 1; and recovering L-tryptophan from the culture.

The culture process in the present invention may be performed in suitable media and culture conditions known in the art. This culture process may be easily modified by any person skilled in the art depending on the type of strain selected. Examples of the culture process include, but are not limited to, batch culture, continuous culture, and fed-batch culture.

The medium and culture conditions that are used in culture of the microorganism of the present invention may be any of those that are generally used in culture of microorganisms of the genus *Escherichia*, but these should properly satisfy the requirements of the microorganism of the present invention.

In a specific embodiment, the microorganism of the present invention may be cultured in a conventional medium containing suitable carbon sources, nitrogen sources, amino acids, vitamins and the like under aerobic conditions while adjusting temperature, pH and the like.

Carbon sources that may be used in the present invention include carbohydrates such as glucose, fructose, sucrose, maltose, mannitol, sorbitol; alcohols and organic acids such as sugar alcohol, glycerol, pyruvic acid, lactic acid and citric acid; and amino acids such as glutamic acid, methionine and lysine, but it's not limited thereto. In addition, natural organic nutrient sources such as starch hydrolysates, molasses, blackstrap molasses, rice bran, cassava, bagasse and corn steep liquor may be used, but it's not limited thereto. Specifically, carbohydrates such as glucose and sterile pretreated molasses (i.e., molasses converted to reduced sugars) may be used, but it's not limited thereto. In addition, suitable amounts of other carbon sources may be used without limitation. Nitrogen sources that may be used in the present invention include inorganic nitrogen sources such as ammonia, ammonium sulfate, ammonium chloride, ammonium acetate, ammonium carbonate, and ammonium nitrate; amino acids such as glutamic acid, methionine and glutamine; and organic nitrogen sources such as peptone, NZ-amine, meat extract, yeast extract, malt extract, corn steep liquor, casein hydrolysate, fish meal or its digested product, defatted soybean cake or its digested product, etc. These nitrogen sources may be used alone or in combination, but it's not limited thereto. The medium may contain, as phosphorus sources, potassium phosphate monobasic, potassium phosphate dibasic and corresponding sodium-containing salts. The medium may contain inorganic compounds may contain sodium chloride, calcium chloride, ferric chloride, magnesium sulfate, ferric sulfate, manganese sulfate and calcium carbonate, but it's not limited thereto. In addition, the medium may contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culture to adjust the pH of the culture medium. In addition, during the culture, a antifoaming agent such as fatty acid polyglycol ester may be used to suppress the formation of bubbles. Further, in order to maintain the culture medium in an aerobic state, oxygen or oxygen-containing gas may be injected into the culture medium. In addition, in order to maintain the culture medium in an anaerobic or non-aerobic state, no gas is injected, or nitrogen, hydrogen or carbon dioxide gas may be injected into the culture medium. The culture medium is typically maintained at a temperature ranging from 27° C. to 37° C., and specifically from 30° C. to 35° C. Culture of the microorganism may be continued until the desired level of the useful substance will be obtained. Specifically, the culture period is may be 10-100 hours.

The method of the present invention may further comprise purifying or recovering the L-tryptophan produced in the culture step. The purification or recovery process may be performed by purifying or recovering the desired L-tryptophan from the culture medium using a suitable method, for example, a batch, continuous or fed-batch culture method.

Hereinafter, the present invention will be described in further detail with reference to examples. It is to be understood, however, that these examples are for illustrative purposes and are not intended to limit the scope of the present invention.

Example 1

Construction of Recombinant Vector Comprising CJ1 Promoter and E. coli trpD Gene or Yeast Trp4 Gene 1-1: Preparation of CJ1 Promoter Fragment In order to obtain a DNA fragment comprising CJ1 promoter, polymerase chain reaction (hereinafter abbreviated as "PCR") was performed using, as a template, a pECCG117-CJ1 plasmid (U.S. Pat. No. 8,048,648) comprising CJ1 promoter. The PCR reaction was performed using a PCR HL premix kit (BIONEER, hereinafter the same) and primers of SEQ ID NOS: 2 and 3 under the following conditions: 30 cycles, each consisting of denaturation at 94° C. for 30 sec, annealing at 55° C. for 30 sec, and elongation at 72° C. for 30 sec.

The PCR product (hereinafter referred to as "PCJ1 fragment") was electrophoresed on 1% agarose gel, and then a band having a desired size was collected by elution.

1-2: Preparation of trpD and Trp4 Gene Fragments

To obtain the ORF of the trpD gene, the W3110 strain derived from wild-type E. coli K-12 was purchased from the Korea Culture Center of Microorganisms, and to obtain the ORF of the trp4 gene, a yeast strain (Saccharomyces cerevisiae) was purchased from the American Type Culture Collection.

From the strains, the genomic DNAs were prepared using a genomic DNA extraction kit (QIAGEN). Using the E. coli genomic DNA as a template, a DNA fragment (1,607 bp) corresponding to the ORF of the trpD gene of SEQ ID NO: 6 was amplified by PCR using primers of SEQ ID NOS: 4 and 5. In addition, using the yeast genomic DNA, a DNA fragment (1,154 bp) corresponding to the ORF of the trp4 gene of SEQ ID NO: 9 was amplified by PCR using primers of SEQ ID NOS: 7 and 8. The PCR products (hereinafter referred to as "trpD fragment" and "trp4 fragment", respectively) were electrophoresed on 0.8% agarose gel, and then bands having a desired size were collected by elution.

1-3: Construction of Recombinant Vectors pCL-$P_{CJ1}$-trpD and pCL-$P_{CJ1}$-Trp4

The $P_{CJ1}$ fragment prepared in Example 1-1 and a pCL1920 vector were treated with the restriction enzyme EcoRI, and then electrophoresed on 0.8% agarose gel. Each of the DNA fragments was ligated into the vector using a rapid DNA ligation kit (ROCHE, hereinafter the same) for 30 minutes, and then transformed into E. coli DH5α cells which were then plated on a spectinomycin-containing LB plate, and the transformed cells were selected.

The selected cells were inoculated into 20 mL of spectinomycin-containing LB liquid medium by a platinum loop and cultured overnight, after which a plasmid DNA was collected using a plasmid extraction kit (QIAGEN, hereinafter the same). The size of the recombinant vector was determined by treatment with the restriction enzyme EcoRI (data not shown), and the clone was identified by performing PCR using primers of SEQ ID NOS: 2 and 3. The recombinant vector was named "pCL-$P_{CJ1}$".

The trpD fragment or trp4 fragment prepared in Example 1-2 and the pCL-$P_{CJ1}$ vector were treated with the restriction enzymes EcoRV and PstI, and then electrophoresed on 0.8% agarose gel. Each of the DNA fragments was ligated into the vector using a rapid DNA ligation kit (ROCHE, hereinafter the same) for 30 minutes, and then transformed into E. coli DH5α cells. The transformed cells were selected in the same manner as described above, and a plasmid DNA was collected in the same manner as described above. The sizes of the recombinant vectors were determined by treatment with the restriction enzymes EcoRI and PstI (data not shown), and the clones were identified by performing PCR using primers of SEQ ID NOS: 2 and 5. The recombinant vectors were "pCL-P$_{CJ1}$-trpD" and "pCL-P$_{CJ1}$-trp4", respectively (FIG. 3).

Example 2

Construction of L-Tryptophan-Producing Strain Transformed with the Recombinant Vector pCL-P$_{CJ1}$-trpD or pCL-P$_{CJ1}$-Trp4

Each of the pCL-P$_{CJ1}$-trpD and pCL-P$_{CJ1}$-trp4 recombinant vectors constructed in Example 1 was introduced into an L-tryptophan-producing parent strain using TSS (transformation and storage solution) reagent supplied by EPICENTRE.

In this Example, E. coli KCCM11166P was used as the L-tryptophan-producing parent strain. E. coli KCCM11166P is an L-tryptophan-producing strain constructed from E. coli KCCM10812P (Korean Patent No. 10-0792095) and is characterized in that the chromosomal tehB gene has been inactivated and the activity of NAD kinase has been increased (Korean Patent Laid-Open Publication No. 10-2012-0083795).

One platinum loop of the L-tryptophan-producing parent strain was inoculated into 4 mL of LB medium and cultured for 3 hours, followed by centrifugation. 50 ng of the pCL-P$_{CJ1}$-trpD vector plasmid or the pCL-P$_{CJ1}$-trp4 vector plasmid and 100 μL of TSS reagent were added to and sufficiently mixed with the separated cells. Next, the cells were introduced into the L-tryptophan-producing parent strain by a one-step transformation technique (Chung et al., Proc Natl Acad Sci USA, 86, 2172-2175, 1989), and the strains were plated on a spectinomycin-containing LB plate, and the transformed strains were selected. To confirm the transformed strains, plasmid DNA was isolated from the transformed strains, and treated with restriction enzymes and subjected to PCR in the same manner as described in Example 1-3. The transformed strains were named "Con/pCL-P$_{CJ1}$-trpD" and "Con/pCL-P$_{CJ1}$-trp4", respectively.

Example 3

Comparison of L-Tryptophan Productivity and Physiological Activity Between Transformed Strains The transformed strains prepared in Example 2 were cultured in Erlenmeyer flasks using the tryptophan titer medium shown in Table 1 below, and the L-tryptophan productivities thereof were analyzed.

TABLE 1

Composition of L-Tryptophan-Producing Medium (per Liter)

| Component | Content (g/L) |
| --- | --- |
| Glucose | 60 |
| KH$_2$PO$_4$ | 0.3 |
| K$_2$HPO$_4$ | 0.6 |
| (NH$_4$)$_2$SO$_4$ | 15 |
| MgSO$_4$·7H$_2$O | 1 |
| Sodium citrate | 5 |
| Yeast extract | 2.5 |
| L-tyrosine | 0.1 |
| L-phenylalanine | 0.15 |
| NaCl | 2.5 |
| Calcium carbonate | 40 |

One platinum loop of each of the L-tryptophan-producing parent strain (Con) and Con/pCL-P$_{CJ1}$-trpD and Con/pCL-P$_{CJ1}$-trp4 strains, cultured overnight in LB solid media in an incubator at 37° C., was inoculated into 25 mL of the titer medium shown in Table 1 above, and then each of the strains was cultured in an incubator at 37° C. and 200 rpm for 40 hours. The results are shown in Tables 2 and 3 below.

TABLE 2

Comparison of Tryptophan Productivity between the L-Tryptophan-Producing Strain and the Strain That Expressed the trpD or trp4 Gene by Vector

| Strain | L-tryptophan (g/L) | anthranilic acid (mg/L) |
| --- | --- | --- |
| Con/pCL | 6.9 ± 0.5 | 722 ± 62 |
| Con/pCL-P$_{CJ1}$-trpD | 8.0 ± 0.4 | 42 ± 13 |
| Con/pCL-P$_{CJ1}$-trp4 | 10.3 ± 2.4 | 28 ± 1 |

TABLE 3

Comparison of Physiological Activity between the L-Tryptophan-Producing Strain and the Strain that Expressed the trpD or trp4 Gene by Vector

| Strain | Cell concentration (OD$_{600}$) | Glucose consumption rate (g/L · h$^{-1}$) |
| --- | --- | --- |
| Con/pCL | 18.2 ± 0.7 | 1.78 ± 0.03 |
| Con/pCL-P$_{CJ1}$-trpD | 19.1 ± 1.4 | 1.76 ± 0.05 |
| Con/pCL-P$_{CJ1}$-trp4 | 20.7 ± 1.5 | 1.67 ± 0.06 |

As can be seen in Table 2 above, the L-tryptophan-producing parent strain produced 6.9 g/L of L-tryptophan during 40 hours of culture, but the Con/pCL-P$_{CJ1}$-trp4 strain and the Con/pCL-P$_{CJ1}$-trp4 produced 8.0 g/L and 10.3 g/L of L-tryptophan, respectively, and thus showed increases in L-tryptophan productivity of 1.1 g/L and 3.4 g/L, respectively, compared to the parent strain (increases of 16% and 49%, respectively).

In addition, as can be seen in Table 3 above, the transformed strains were similar to the L-tryptophan-producing parent strain in terms of glucose consumption rate or cell growth, and the accumulation of the fermentation byproduct acetate in the transformed strain was also similar to or lower than that in the L-tryptophan-producing parent strain (data not shown). Thus, it could be seen that the transformed strains showed physiological activity substantially similar to the L-tryptophan-producing parent strain.

Particularly, in the L-tryptophan-producing parent strain, the phenomenon that normal fermentation is not maintained due to abnormal fermentation involving the accumulation of anthranilic acid during fermentation often appears. Thus, in fermentation of the L-tryptophan-producing parent strain, it is important to control fermentation factors so as to prevent the excessive accumulation of anthranilic acid, and continuous monitoring is disadvantageously required. Thus, an L-tryptophan-producing strain in which anthranilic acid is less accumulated is considered important in that it can lower the frequency of abnormal fermentation. As can be seen in Tables 2 and 3, the transformed strains that expressed the trpD or trp4 gene by the pCL vector showed a lower accumulation of anthranilic acid compared to the L-tryptophan-producing strain.

From a comparison between the transformed strains that express *E. coli* anthranilate phosphoribosyltransferase and yeast anthranilate phosphoribosyltransferase, respectively, it could be seen that the transformed strain expressing the trp4 gene having high affinity for PRPP was better in terms of an increase in L-tryptophan productivity and a decrease in the accumulation of anthranilic acid.

Thus, it can be concluded that, when the transformed strain expressing the trp4 gene is used to produce L-tryptophan, L-tryptophan can be produced with higher productivity and the overall productivity of L-tryptophan can be maintained at a high level by maintaining higher fermentation stability.

Example 4

Transformation of Recombinant Vector pCL-P$_{CJ1}$-Trp4 into L-Tryptophan-Producing Strains and Comparison of L-Tryptophan Productivity Between Transformed Strains In order to examine whether the effect described in Example also appears in other L-tryptophan-producing strains, the pCL-P$_{CJ1}$-trp4 vectors were transformed into the strains, and L-tryptophan productivity was compared between the transformed strains in the same manner as described in Example 3.

The L-tryptophan-producing *E. coli* strains used in this Example were KCCM10805P (Korean Patent No. 0850853) and KCCM10814P (Korean Patent No. 0838036). The KCCM10805P *E. coli* mutant strain is an L-tryptophan-producing *E. coli* strain derived from the L-tryptophan-producing *E. coli* strain CJ285 (Korean Patent Publication No. 10-2005-0059685) having resistance to the tryptophan analogue tryptophan hydroxamate and is characterized in that the nrfE gene that is involved in nitrite reduction has been inactivated by homologous recombination. The KCCM10814P *E. coli* mutant strain is an L-tryptophan-producing *E. coli* strain derived from CJ285 and is characterized in that the yjeO gene encoding a protein required to synthesize an inner membrane has been deleted.

4-1: Construction of Various L-Tryptophan-Producing Strains Transformed with Recombinant Vector pCL-P$_{CJ1}$-Trp4

The recombinant vector pCL-P$_{CJ1}$-trp4 was introduced into the L-tryptophan-producing strains KCCM10805P and KCCM10814P in the same manner as described in Example 2 to construct transformed strains. The transformed strains were named "KCCM10805P/pCL-P$_{CJ1}$-trp4" and "KCCM10814P/pCL-P$_{CJ1}$-trp4", respectively.

4-2: Comparison of L-Tryptophan Productivity Between Various L-Tryptophan-Producing Strains Transformed with Recombinant Vector pCL-P$_{CJ1}$-Trp4

The transformed strains constructed in Example 4-1 above were cultured in Erlenmeyer flasks in the same manner as described in Example 3, and the L-tryptophan productivities thereof were compared. The results of the comparison are shown in Table 4 below.

TABLE 4

| Strain | L-tryptophan (g/L) | Anthranilic acid (mg/L) |
|---|---|---|
| Con/pCL | 6.5 ± 0.5 | 833 ± 100 |
| Con/pCL-P$_{CJ1}$-trp4 | 10.2 ± 0.5 | 45 ± 12 |
| KCCM10805P | 8.7 ± 0.3 | 356 ± 82 |
| KCCM10805P/pCL-P$_{CJ1}$-trp4 | 9.6 ± 0.6 | 67 ± 12 |
| KCCM10814P | 8.2 ± 0.9 | 484 ± 114 |
| KCCM10814P/pCL-P$_{CJ1}$-trp4 | 9.8 ± 0.5 | 63 ± 11 |

As can be seen in Table 4 above, when the yeast trp4 gene was expressed in the three L-tryptophan-producing strains by the vectors, the L-tryptophan productivity was increased by about 0.9-3.7 g/L. In addition, it was shown that, when the east trp4 gene was expressed in the three L-tryptophan-producing strains by the vectors, the amount of anthranilic acid greatly decreased. This suggests that expression of the yeast trp4 gene in the L-tryptophan-producing strain has the effects of enhancing the L-tryptophan productivity of the strain while suppressing the accumulation of anthranilic acid in the strain.

Example 5

Construction of Recombinant L-Tryptophan-Producing Strain Having the CJ1 Promoter and Trp4 Gene Introduced into Chromosome of L-Tryptophan-Producing Strain In the Con/pCL-P$_{CJ1}$-trp4 strain constructed in Example 3, the transformed strain can lose the plasmid during cell division, and thus can lose the trp4 gene expression cassette. In this case, the transformed strain is returned to the L-tryptophan-producing strain, indicating that it is difficult to stably maintain the trp4 gene expression cassette. In addition, there is a risk in that the antibiotic-resistant selection marker in the plasmid can be introduced into the genome of the L-tryptophan-producing parent strain to generate a mutant strain having resistance to the antibiotic.

For this reason, in the present invention, only the trp4 gene expression cassette was inserted into the ybiX gene locus in the genome of the L-tryptophan-producing parent strain in order to solve this problem.

5-1: Construction of Vector Comprising P$_{CJ1}$-Trp4 Fragment and Chloramphenicol Acetyltransferase Gene As a selection marker for confirming insertion of the trp4 gene expression cassette into the genome, the chloramphenicol acetyltransferase gene imparting resistance to chloramphenicol was used. For this, a pUCprmfmloxC vector (Korean Patent Laid-Open Publication No. 2009-0075549) comprising the chloramphenicol acetyltransferase gene was used.

Using pCL-P$_{CJ1}$-trp4 constructed in Example 1-3 as a template, PCR was performed with primers of SEQ ID NOS: 10 and 11 to prepare a P$_{CJ1}$-trp4 fragment. The prepared fragment and the pUCprmfmloxC vector were treated with the restriction enzymes KpnI and SpeI, and then electrophoresed on 0.8% agarose gel. Each of the DNA fragments was ligated into the vector using a rapid DNA ligation kit (ROCHE, hereinafter the same) for 30 minutes, and then transformed into *E. coli* DH5α cells. The transformed cells were selected on a chloramphenicol-containing LB solid medium. The selected colony was cultured in LB liquid medium, and the plasmid DNA was recovered, treated with a restriction enzyme, and sequenced to confirm that a vector comprising the P$_{CJ1}$-trp4 gene and the chloramphenicol acetyltransferase gene was properly constructed. The confirmed vector was named "pmlox-Cmt-P$_{CJ1}$-trp4".

5-2: Preparation of DNA Fragment for Inserting DNA Fragment Comprising P$_{CJ1}$-Trp4 Gene and Chloramphenicol Acetyltransferase Gene into ybiX Gene Locus The ybiX gene (Gene ID: 12930961) is a gene whose function has not yet been clearly elucidated, and it is known that deletion of the gene leads to an increase in the intracellular level of ATP (Hara et al., *FEMS Microbiol Lett*, 297, 217-224, 2009). It is known that, even when the ybiX gene is deleted from an *E. coli* strain, the physiological activity of the *E. coli* strain is not greatly influenced. Thus, in the present invention, the trp4 gene expression cassette was inserted onto the ybiX gene locus in the genome of the L-tryptophan-producing parent strain.

A trp4 expression cassette fragment to be inserted onto the ybiX gene locus was prepared by performing PCR using the pmlox-Cmt-P$_{CJ1}$-trp4 plasmid, constructed in Example 5-1, as a template and primers of SEQ ID NOS: 12 and 13. The prepared DNA fragment was electrophoresed on 0.8% agarose gel. Using the electrophoresed DNA fragment as a template, PCR was performed again with primers of SEQ ID NOS: 14 and 15. The resulting DNA fragment was electrophoresed on 0.8% agarose gel.

The prepared DNA fragment is a fragment comprising a 100-bp sequence equal to the ybiX gene at each of the 5' and 3' ends, and can be inserted into the ybiX gene locus in the genome of the L-tryptophan-producing strain by recombinase. The concentration of the prepared DNA fragment was measured using NanoDrop (Thermo SCIENTIFIC). The prepared DNA fragment was named "ybiX::Cm-P$_{CJ1}$-trp4", and the sequence thereof is represented by SEQ ID NO: 16.

5-3: Insertion of Yeast Anthranilate Phosphoribosyltransferase Expression Cassette of P$_{CJ1}$-Trp4 into ybiX Gene Locus of L-Tryptophan-Producing Strain The trp4 gene expression cassette was inserted into the ybiX gene locus by recombinase. For this insertion, the one-step inactivation technique using lambda Red recombinase developed by Datsenko K A et al. was used (Datsenko et al., *Proc Natl Acad Sci USA*, 97, 6640-6645, 2000).

The pKD46 vector plasmid expressing lambda Red recombinase was transformed into the L-tryptophan-producing strain (KCCM 10812P) in the same manner as described in Example 2. The L-tryptophan-producing strain transformed with the pKD46 vector was selected on an ampicilin-containing LB solid medium. To induce the expression of lambda Red recombinase, the selected L-tryptophan-producing strain transformed with the pKD46 vector was cultured in 20 mL of a liquid LB medium containing 5 mM of arabinose. When the concentration of the cells reached 5×10$^8$ cells/mL, the cells were recovered and washed three times with a 10% cold glycerol solution.

500 ng of the ybiX::Cm-P$_{CJ1}$-trp4 DNA fragment prepared in Example 5-2 was introduced into the resulting L-tryptophan-producing strain by electroporation. In the L-tryptophan-producing strain having the DNA fragment introduced therein, the chloramphenicol-resistant gene and the trp4 gene expression cassette were inserted into the ybiX gene locus by homologous recombination caused by lambda Red recombinase. Because this strain showed resistance to chloramphenicol, it was selected on a chloramphenicol-containing LB solid medium. The selected strain was subjected to colony PCR using primers of SEQ ID NOS: 17 and 18, and as a result, it was confirmed that the Cm-P$_{CJ1}$-trp4 fragment was inserted into the ybiX gene locus of the strain.

Because the pKD46 vector had a temperature-sensitive replication origin, the selected strain was then incubated at a temperature of 40° C. or higher to remove the pKD46 vector from the cells. This removal was confirmed by the fact that the selected strain did not grow on an ampicillin-containing solid LB medium.

Next, in order to remove the chloramphenicol-resistant gene from the genome of the L-tryptophan-producing strain, a pJW168 plasmid (Palmeros et al., *Gene*, 247, 255-264, 2000) was introduced into the strain in the same manner as described in Example 2. In order to express Cre-recombinase from the introduced pJW168 plasmid, isopropyl-β-D-1-thiogalactopyranoside (IPTG) was plated on an ampicillin-containing solid LB medium, and a strain was selected. In the selected strain, the chloramphenicol-resistant gene was removed by genetic recombination caused by Cre-recombinase at the mutant loxP position, and this removal was confirmed using primers of SEQ ID NOS: 17 and 18. The strain confirmed as described above was an L-tryptophan-producing strain having the trp4 gene expression cassette inserted therein and was named "Con/ybiX::P$_{CJ1}$-trp4".

Example 6

Comparison of L-Tryptophan Productivity and Physiological Activity of Transformed Strain Having Trp4 Gene Expression Cassette Inserted into Chromosome The transformed strain prepared in Example 5 was cultured in an Erlenmeyer flask using the tryptophan titer medium shown in Table 1 above, and the L-tryptophan productivity thereof was analyzed.

One platinum loop of each of the L-tryptophan-producing parent strain (Con) and Con/ybiX::P$_{CJ1}$-trp4 strain cultured overnight on an LB solid medium in an incubator at 37° C. was inoculated into 25 mL of the titer medium shown in Table 1 above, and was then cultured in an incubator at 37° C. and 200 rpm for 40 hours. The results of the culture are shown in Tables 5 and 6 below.

TABLE 5

Comparison of Tryptophan Productivity between the L-Tryptophan-Producing Parent Strain and the Strain having the trp4 Gene Expression Cassette Inserted into the Chromosome

| Strain | L-tryptophan (g/L) | Anthranilic acid (mg/L) |
|---|---|---|
| Con | 6.3 ± 1.5 | 579 ± 32 |
| Con/ybiX::P$_{CJ1}$-trp4 | 9.5 ± 1.2 | 31 ± 18 |

TABLE 5

Comparison of Physiological Activity between the L-Tryptophan-Producing Parent Strain and the Strain having the trp4 Gene Expression Cassette Inserted into the Chromosome

| Strain | Cell concentration (OD$_{600}$) | Glucose consumption rate (g/L · h$^{-1}$) |
|---|---|---|
| Con | 17.7 ± 1.3 | 1.50 ± 0.08 |
| Con/ybiX::P$_{CJ1}$-trp4 | 19.3 ± 1.6 | 1.54 ± 0.07 |

As can be seen in Table 5 above, the parent strain produced 6.3 g/L of L-tryptophan during 40 hours of culture, but the Con/ybiX::P$_{CJ1}$-trp4 strain produced 9.2 g/L of L-tryptophan, and thus showed an increase in L-tryptophan productivity of 2.9 g/L (46% increase) compared to the parent strain.

In addition, as can be seen in Table 6 above, the Con/ybiX::P$_{CJ1}$-trp4 strain was similar to the parent strain in terms of glucose consumption rate and cell growth, like the transformed strain having the trp4 gene expression cassette introduced by the vector. Further, the accumulation of the fermentation byproduct acetate in the Con/ybiX::P$_{CJ1}$-trp4 strain was similar to or lower than that in the parent strain (data not shown).

Thus, it could be seen that the Con/ybiX::P$_{CJ1}$-trp4 strain showed physiological activity substantially similar to that of the L-tryptophan-producing parent strain, like the transformed strain having the transformed strain having the trp4 gene expression cassette introduced by the vector. In addition, it was observed that the accumulation of anthranilic acid in the Con/ybiX::P$_{CJ1}$-trp4 strain during fermentation greatly decreased compared to that in the L-tryptophan-producing parent strain, like the case of the transformed strain having the transformed strain having the trp4 gene expression cassette introduced by the vector. Therefore, it can be concluded that, when the Con/ybiX::P$_{CJ1}$-trp4 strain is used to produce L-tryptophan, L-tryptophan can be produced with higher productivity and the overall productivity of L-tryptophan can be maintained at a high level by maintaining higher fermentation stability.

Accession Number

Depository authority: Korean Culture Center of Microorganisms;

Accession number: KCCM11408P;

Deposit date: Apr. 8, 2013.

---

The invention claimed is:

1. An L-tryptophan producing recombinant microorganism of the genus *Escherichia* having enhanced L-tryptophan productivity relative to a non-modified microorganism, wherein the recombinant microorganism has been modified to express yeast anthranilate phosphoribosyltransferase.

2. The L-tryptophan producing recombinant microorganism of the genus *Escherichia* according to claim 1, wherein the yeast anthranilate phosphoribosyltransferase has the amino acid sequence represented by SEQ ID NO: 1.

3. The L-tryptophan producing recombinant microorganism of the genus *Escherichia* according to claim 1, wherein the modification is achieved either by transformation with a vector comprising a polynucleotide encoding the anthranilate phosphoribosyltransferase or by insertion of the polynucleotide into a chromosome.

4. The L-tryptophan producing recombinant microorganism of the genus *Escherichia* according to claim 3, wherein the polynucleotide has the nucleotide sequence represented by SEQ ID NO: 9.

5. The L-tryptophan producing recombinant microorganism of the genus *Escherichia* according to claim 1, wherein the microorganism of the genus *Escherichia* is *Escherichia coli*.

6. A method for producing L-tryptophan, comprising the steps of:
   culturing a L-tryptophan producing recombinant microorganism of the genus *Escherichia* having enhanced L-tryptophan productivity relative to a non-modified microorganism of claim 1; and
   recovering L-tryptophan from the culture.

* * * * *